United States Patent [19]

Preston

[11] 4,438,096

[45] Mar. 20, 1984

[54] PEARLESCENT SHAMPOO

[75] Inventor: John C. Preston, Chicago, Ill.

[73] Assignee: Helene Curtis Industries, Inc., Chicago, Ill.

[21] Appl. No.: 382,421

[22] Filed: May 27, 1982

[51] Int. Cl.³ .............................................. A61K 7/06
[52] U.S. Cl. .............................. 424/70; 424/DIG. 2; 424/DIG. 4
[58] Field of Search ........................................... 424/70

[56] References Cited

U.S. PATENT DOCUMENTS

| | | | |
|---|---|---|---|
| 3,808,329 | 4/1974 | Bolich, Jr. et al. | 424/70 |
| 3,829,563 | 8/1974 | Barry et al. | 424/70 |
| 4,076,800 | 2/1978 | Marsh et al. | 424/70 |
| 4,087,518 | 5/1978 | Smith et al. | 424/70 |

FOREIGN PATENT DOCUMENTS 1124842  8/1968  United Kingdom .................. 424/70

OTHER PUBLICATIONS

Konetzke et al., Chem. Abs., 1967, vol. 66, pp. 65015r.
Ash et al., A Formulary of Cosmetic Preparations, 1977, pp. 27, 28, 37–39, 41–43, 51–53, 74, 80, 81.

*Primary Examiner*—Dale R. Ore
*Attorney, Agent, or Firm*—Dressler, Goldsmith, Shore, Sutker & Milnamow, Ltd.

[57] ABSTRACT

The present invention relates to pearlescent shampoos in which the pearlescing agent is myristyl myristate and is present in the shampoo in an amount of about 0.2 to about 2.5 weight percent. Also included in the shampoo are water and an amount of surface active agent effective for cleansing.

17 Claims, No Drawings

PEARLESCENT SHAMPOO

DESCRIPTION

1. Technical Field

The present invention relates to shampoo compositions, and particularly to pearlescent shampoos that contain myristyl myristate as the pearlescing agent.

2. Background Art

Cosmetic compositions, simulated pearls and lacquers may contain a lustrous, silvery-white substance to impart a pearl-like quality or pearlescence to the composition. Several materials are known to be useful for creating pearlescence.

Those materials derived from naturally occuring and inorganic materials include comminuted fish scales, mica, mercuric chloride and shell fish nacres. Ethylene glycol monostearate and ethylene glycol distearate are also frequently utilized.

The known pearlescent materials suffer from several disadvantages. For example, non-separating, stable pearlescent compositions that contain a relatively large amount of water, such as shampoos, have been difficult to prepare. That is, once prepared, such compositions tend to separate into two phases, one of which contains a large amount of the pearlescent material.

Cosmetic compositions that contain ethylene glycol monostearate or distearate as a pearlescing agent can be made relatively stable to phase separation at ambient temperatures. However, when the temperature of the composition is raised above the melting point of the pearlescer, as can occur during summer storage of a product, the composition must be cooled with agitation to be returned to a pearlescent condition.

Ethylene glycol monostearate and distearate are each typically utilized at about 1.5 to about 3.5 weight percent of shampoo compositions as a pearlescent agent. When so used, those pearlescers tend to interfere with lathering.

Another disadvantage of some of the known pearlescent materials such as comminuted fish scales, mica or shell fish nacre is that the particulate pearlescers can be abrasive when used in a shampoo that is to be rubbed on the scalp and hair.

SUMMARY OF THE INVENTION

The present invention relates to improved pearlescent shampoos which contain a novel pearlescent agent; namely, myristyl myrsitate that is present in the shampoo in an amount of about 0.2 to about 2.5 weight percent of the shampoo.

The present invention has several benefits and advantages. One such benefit is that pearlescent shampoos can be prepared that remain substantially homogeneous, and do not separate into distinct phases at ambient temperatures.

Another benefit of this invention is that these shampoos return to a pearlescent condition after heating to a temperature above the melting point of myristyl myristate without the need of cooling with agitation.

A further benefit of this invention is that myristyl myristate does not interfere with lathering of the shampoo as do ethylene glycol monostearate and disterate when present in amounts sufficient to pearlesce.

Another advantage of this invention is that hair fibers shampooed with a shampoo of this invention exhibit improved strength over hair fibers shampooed with a shampoo in which water is used to replace myristyl myristate.

Yet another benefit of the present invention is that the myristyl myristate is not abrasive to the hair or scalp during the shampooing process as are comminuted, particulate perlescers such as mica and fish scales.

Still further benefits and advantages of the present invention will be apparent to those skilled in the art from the description of the invention, examples and claims that follow.

DETAILED DESCRIPTION OF THE INVENTION

The present invention relates to aqueous shampoo compositions that are pearlescent. The pearlescence in these compositions is achieved through a novel pearlescing agent; i.e., myristyl myristate. A particularly preferred myristyl myristate is that sold under the trademark CERAPHYL 424 by Van Dyk and Company, Inc. of Belleville, N.J.

The myristyl myristate is preferably present in the shampoos in an amount of about 0.2 to about 2.5 weight percent of the entire composition. More preferably, the ester is present at about 0.25 to about 2 weight percent. For stable, non-separating compositions that are substantially free from phase-stabilizing ingredients, the myristyl myristate is most preferably present in an amount of 0.25 to about 1 weight percent of the shampoo compositions.

The lower limit of myristyl myristate appears to be of import to the pearlescence of the shampoo of this invention, while the upper limit relates more to convenience.

Thus, when myristyl myristate was present in a shampoo at an amount of about 0.1 weight percent, no pearlescence was observed, even after a period of several weeks. At about 0.2 weight percent, pearlescence was observed after a period of about two weeks. When used at the more preferred levels of 0.25 and 0.5 weight percents, pearlescence was noted after several days, and one day, respectively.

When myristyl myristate was utilized in an amount of 1.25 weight percent of the shampoo, pearlescence developed as the preparation of the shampoo was completed, with phase separation being noted after a two week period at ambient temperature. Greater quantities of myristyl myristate provide pearlescence, but lead to more rapid phase separation, unless an additional ingredient is added to the composition, as discussed hereinafter. Quantities of myristyl myristate greater than about 2.5 weight percent of the shampoo composition provides pearlescent compositions, but it is wasteful to use such quantities.

The amount of cleansing, surface active agent (discussed hereinafter) present in the shampoo can affect the amount of myristyl myristate that is utilized in preparing a homogeneous shampoo with use of greater amounts of surface active agent favoring greater stability. Selection of a specific amount of myristyl myristate is, however, well within the skill of those skilled in formulating cosmetic compositions.

Myristyl myristate is suggested for use in providing a velvety skin feel and as a viscosity builder that is superior to cetyl alcohol in lotions. In emulsified make-up products, it is said to improve spreading, and in hand and body lotions of high water content, it is said to provide a richness equivalent to having doubled the oil phase. Pearl effects are also noted by the manufacturer in certain soap systems when myristyl myristate is used in excess of 3.5 percent; i.e. at more than 140 percent of the maximum amount utilized herein.

It is noted that myristyl myristate appears to be a singular pearlescing agent in the group of fatty alcohol esters of fatty acids. For example, cetyl palmitate does not form a pearlescent shampoo when used as a replacement for myristyl myristate. This was quite suprising since cetyl palmitate is a homologous ester of myristyl myristate in that it contains sixteen carbon atoms in each of the alcohol and acid portions of the ester while myristyl myristate contains fourteen carbon atoms in each portion of the ester. In addition, both esters are crystalline solids with melting points in excess of about 35° C.

Particularly preferred shampoos of this invention are substantially stable to phase separation of the myristyl myristate from the remainder of the composition. In these compositions, the concentration of myristyl myristate is about 0.25 to about 1 weight percent of the total composition when the aforementioned additional phase-stabilizing ingredient is substantially absent from the composition, and at about 0.25 to about 2 weight percent when that ingredient is present, as discussed below.

The additional phase-stabilizing ingredient that retards phase separation for the higher quantities of myristyl myristate is a thickening agent that is a water-dispersible alkyl and hydroxyalkyl substituted polysaccharide wherein the alkyl substituent is selected from the group consisting of methyl and ethyl, and the hydroxyalkyl substituent is selected from the group consisting of 2-hydroxyethyl, 2-hydroxypropyl and 2-hydroxybutyl. In preferred practice, this phase-stabilizing ingredient is a cellulose derivative containing methyl and 2-hydroxypropyl substituents on the anhydroglucose rings of the cellulose, hereinafter referred to as the "cellulosic thickener."

Several preferred cellulosic thickeners are available commercially. Particularly preferred among these thickeners are the cellulose derivatives sold under the trademarks METHOCEL J5MS and METHOCEL E4M by the Dow Chemical Company. METHOCEL J5MS is reported by its manufacturer to contain about equal amounts of methyl and 2-hydroxypropyl substituents on the anhydroglucose rings. METHOCEL E4M is reported to have methyl groups or about 80 to 95 percent of the ring substituents, with hydroxypropyl groups constituting the remaining ring substituents.

The particularly preferred cellulosic thickening agent is utilized in an amount of about 0.25 to about 1.5 weight percent of the composition. More preferably, this thickener is present at about 0.5 to about 1 weight percent.

The class of cellulosic thickeners useful herein are known to be useful in thickening aqueous compositions, and the particularly preferred cellulosic thickener is used, in part, as a thickener herein. However, the particularly preferred cellulosic thickeners used herein not only thicken the shampoos, but also act to stabilize the pearlescent shampoo and retard the phase separation of the composition when amounts of myristyl myristate in excess of about 1 weight percent of the composition are utilized.

In addition to water, which can comprise about 75 to about 90 weight percent of the shampoo composition, myristyl myristate and optional cellulosic thickener, the shampoo composition of this invention contains an amount of surface active agent that is effective for cleansing. Useful surface active agents are typically present in an amount of about 5 to about 20 weight percent of the composition.

The surface active agent can be anionic, cationic, nonionic, zwitterionic or amphoteric. Typically useful surface active agents contain least one fatty, carbon atom, chain. The individual surface active agents can also be used in mixtures of two or more surface active agents or their salts.

Exemplary anionic surface active agents include but are not limited to alkali metal and ammonium salts of fatty alkyl sulfates and fatty alpha-olefin sulfonates such as ammonium lauryl sulfate and the sodium alpha-olefin sulfonate prepared from mixed olefins having about 12 to 18 carbon atoms in the fatty chain, alkali metal and ammonium soaps such as potassium oleate and ammonium palmitate, alkali metal ethoxylated fatty alkanol sulfates and phosphates such as sodium polyoxyethylene myristyl sulfate and potassium polyoxyethylene lauryl phosphate in which there are an average of 1 to about 4 oxyethylene units per molecule, and the like.

Exemplary nonionic surface active agents include but are not limited to polyoxyethylene derivatives of fatty alcohols containing about 4 to about 25 oxyethylene units per molecule such as polyoxyethylene (20) cetyl ether and polyoxyethylene (4) lauryl ether, polyoxyethylene derivatives of octyl- and nonylphenols containing an average of about 4 to about 25 oxyethylene units such as polyoxyethylene (9) octylphenyl ether and polyoxyethylene (15) nonylphenyl ether, mono- and dialkanol amides of fatty acids such as N-(2-hydroxyethyl) tallow acid amide and N,N-bis-(2-hydroxyethyl) coco fatty acid amide, and the like.

It is noted that N,N-bis-(2-hydroxyethyl)coco fatty acid amide is used herein as a foam booster (discussed hereinafter). While being a foam booster, this compound is also a nonionic surface active agent, and as such, it is included in the total amount of surface active agent.

Exemplary cationic surface active agents include but are not limited to quaternary nitrogen-containing compounds that include the following structures: (1) one fatty chain and three lower alkyl (one to four carbon atoms) substituents on the quaternary nitrogen such as stearyltrimethylammonium chloride and cetyldimethylethylammonium bromide; (2) one fatty chain, two lower alkyl groups and a benzyl group such as cetyldimethylbenzylammonium bromide; (3) two fatty chains and two lower alkyl groups such as dimethyldi-(hydrogenated tallow)-ammonium chloride; and the like.

Exemplary zwitterionic surface active agents include but are not limited to betaine and sultaine derivatives such as stearyldimethylglycine, cocamidopropyldimethylglycine, cocamidopropyldimethyl sultaine, and the like, as well as fatty tertiary amine oxides such as dimethylcocoamine oxide and dimethylstearylamine oxide.

Illustrative amphoteric surface active agents include but are not limited to fatty chain derivatives of mono- and dicarboxy substituted imidazolines such as 2-heptadecyl-1-carboxymethyl-1-(2-hydroxyethyl)-2-imidazolinium chloride, 2-undecyl-1-(sodium carboxymethyl)-1-(2-hydroxyethyl)-2-imidazolinium hydroxide. Also included among the amphoteric surface active agents are fatty derivatives of glycine such as lauryl aminopropylglycine.

Anionic surface active agents such as alkali metal and ammonium lauryl sulfate or alpha-olefin sulfonate prepared from mixed olefins having about 14 to about 16 carbon atoms in the fatty chain are particularly preferred. These particularly preferred surfactants are preferably utilized at about 7 to about 17 weight percent of the composition.

A foam booster, such as an N,N-bis-(2-hydroxyethyl) coco fatty acid amide, is also useful herein as part of the surface active agent system. Similar compounds, like N,N-bis-(2-hydroxyethyl)lauramide, are also useful. These foam boosters are typically utilized in an amount of about 0.5 to about 4 weight percent of the composition, and more preferably at about 2.5 to about 3.5 weight percent, and are considered as part of the total amount of surface active agent.

The word "fatty" is used herein to refer to carbon atom chains that contain about 12 to about 18 carbon atoms. The word "fatty" is also used in conjunction with carbon atom chains that are derived from chains of about 12 to about 18 carbon atoms, wherein at least one atom of the chain is within a ring structure, rather than being pendant from that ring structure, as is the case for one imidazoline derivative discussed hereinbefore.

The shampoo compositions of this invention can be utilized as prepared with the previously mentioned components. However, it is preferred that a further, thickening, viscosity-building agent be added to the shampoo in addition to the before discussed cellulosic thickener to adjust the viscosity to about 1500 to about 5000 centipoises measured at 80° F. (about 28° C.), and more preferably to be about 2000 to about 3500 centipoises.

The preferred, additional, viscosity-building agent is a salt such as sodium chloride or ammonium chloride. The specific amount of viscosity-building salt that is useful for a shampoo of this invention is a function of the selection and amount of the particular ingredients present. However, the adjustment of viscosity by admixture of salts is also well known and within the skill of those used to preparing shampoos.

The pH value of the compositions of this invention is preferably about 4 to about 9, and more preferably about 5 to about 7.

Additional ingredients such as colorants, perfumes, preservatives, cosmetic oils, sequesterants and the like can also be incorporated into the shampoo of this invention.

The shampoo of this invention can be prepared by providing a liquid medium that contains water and an amount of surface active agent effective for cleansing. In preferred practice, the liquid medium also includes the water-dispersible cellulosic thickener.

The myristyl myristate is admixed with the liquid medium while the ester is in a liquid state. A liquid state of the myristyl myristate can be achieved by admixing the solid compound with a liquid medium that is heated to a temperature above the myristyl myristate melting point and maintained at that temperature during the admixture. The myristyl myristate can alternatively be melted and admixed while at a temperature above its melting point and maintained in the liquid state during that admixture.

It is particularly preferred that both the liquid medium and myristyl myristate be heated to a temperature above the melting point of myristyl myristate prior to and during admixture. Myristyl myristate melts at about 36°–39° C. and it is preferably admixed with the liquid medium at a temperature for each of at least about 110° F. (about 44° C.).

Once the liquid myristyl myristate and liquid medium are admixed, the resulting admixture is agitated until a substantially homogeneous, substantially visible light transparent admixture is obtained. It is thought that a solution of the ester, or a dispersion of very finely divided liquid ester, is formed in the liquid medium at this stage of the method.

The temperature of the transparent admixture is then reduced to ambient to form the pearlescent shampoo. Temperature reduction is thought to lead to crystallization of the ester to effect the observed pearlescence.

It is noted that crystallization normally leads to precipitation or phase separation of the crystals so produced. Here, however, cooling and presumed crystallization typically does not lead to phase separation of the myristyl myristate from the liquid medium unless the myristyl myristate is present in an amount greater than about 1 percent by weight of the shampoo and the cellulosic thickener is absent or present in an insufficient amount to prevent phase separation.

The present invention is further illustrated in the examples that follow.

BEST MODE FOR CARRYING OUT THE INVENTION

Example 1: Pearlescent Shampoo

A pearlescent shampoo of this invention was prepared as follows:

| Ingredients | Weight Percent |
|---|---|
| 1. Water | 58.90 |
| 2. Cellulosic thickener[1] | 1.00 |
| 3. Tetrasodium ethylenediaminetetraacetic acid (39 percent active) | 0.20 |
| 4. Ammonium lauryl sulfate (30 percent active) | 35.00 |
| 5. Myristyl myristate | 0.60 |
| 6. Fatty acid diethanolamide[2] | 3.00 |
| 7. Perfume | 0.25 |
| 8. Ammonium chloride | 0.80 |
| 9. Citric acid (50 percent active) | 0.20 |
| 10. Preservative | 0.05 |
| 11. Colorant | Q.S. |
|  | 100.00 |

[1]The cellulosic thickener used was METHOCEL J5MS sold by The Dow Chemical Company.
[2]N,N—(2-hydroxyethyl)coco fatty acid amide was used.

Components 1 and 2 were stirred until a substantially homogeneous admixture resulted. Component 3 was added with further stirring until the resulting admixture was clear. Component 4 was added and the resulting liquid medium was stirred with heating until a temperature of 150° F. was reached. Component 8 was added thereafter with sufficient stirring to affect dissolution. Component 5 was then added with stirring, the resulting admixture was heated to a temperature of 155° F. and the stirring was continued until a substantially homogeneous, substantially visible light transparent admixture was obtained.

The homogeneous, transparent admixture was then cooled and components 6 and 9 were added with stirring until substantial homogeneity was obtained. The cooled admixture was then reduced to a temperature of about 120° F. at which temperature components 7, 10 and 11 were added with sufficient stirring to obtain substantial homogeneity. The pH value was then adjusted to be about 6.1-6.3. Further temperature reduction to ambient produced pearlescence in the shampoo. A viscosity of 3700 centipoises at 80° F. was found for this shampoo.

It was noted that the shampoo was translucent with some pearl being exhibited at a temperature of 102° F. When the pearlescent shampoo of this Example was subsequently warmed to 135° F. it became clear. Reduction in temperature to ambient thereafter returned the pearlescence after a period of about two days without the need for additional agitation.

The composition of this Example performed as a shampoo when used to treat human hair.

Example 2: Concentration Study for Pearlescent Shampoos

A series of eight shampoos labeled A through H were prepared to study the effect of the amount of pearlescing ester in the shampoo upon pearlescence itself, and upon phase separation of the pearlescent ester from the liquid medium of the shampoo. The shampoos were prepared in a manner substantially similar to that used in Example 1.

The basic shampoo composition, Shampoo A, had the following ingredients, with water being replaced by successive amounts of myristyl myristate for shampoos B through H.

| Ingredients | Weight Percent |
| --- | --- |
| Water | Q.S. to 100 |
| Cellulosic thickener[1] | 0.0001 |
| Ammonium lauryl sulfate (30 percent active) | 19.00 |
| Sodium lauryl sulfate (30 percent active) | 19.00 |
| Tetrasodium ethylenediaminetetraacetic acid (39 percent active) | 0.20 |
| Fatty acid diethanolamide[2] | 2.50 |
| Citric acid (50 percent active) | 0.07 |
| Ammonium chloride | 1.10 |
| Perfume | 0.30 |
| Colorant | Q.S. |
| Preservative | Q.S. |
| | 100.00 |

[1]The cellulosic thickener used was METHOCEL J5MS sold by The Dow Chemical Company.
[2]N,N—(2-hydroxyethyl)coco fatty acid amide was used.

The amount of myristyl myristate (MM), viscosities and comments noted for each of shampoos B through H are shown in Table 1 below.

TABLE 1

| | Shampoos B through H | | |
| --- | --- | --- | --- |
| Shampoo | Weight Percent MM[1] | Viscosity[2] (centipoises) | Comments |
| B | 0.10 | 3000 | Shampoo remains clear. |
| C | 0.20 | — | Slight pearlescence after two weeks. |
| D | 0.25 | — | Pearlescence after several days; stable. |
| E | 0.50 | 3200 | Pearlescence within 1 day; stable. |
| F | 0.75 | 3400 | Pearlescence within 1 day; stable. |
| G | 1.00 | 2250 | Pearlescence within 1 day; stable. |
| H | 1.25 | 1500 | Pearlescence at end of preparation, slight separation after 2 weeks. |

[1]MM stands for myristyl myristate.
[2]Viscosities were measured at 80° F. one day after preparation.

A composition similar to that of shampoo A was prepared that contained 0.50 weight percent of the cellulosic thickener, 1.50 weight percent myristyl myristate and an additional amount of ammonium chloride sufficient to adjust the viscosity to between 2500 and 3500 centipoises, at 80° F. This shampoo did not exhibit phase separation and showed good pearlescence.

The results of the above studies illustrate the approximate minimum amount of myristyl myristate required to exhibit pearlescence in the shampoo, the phase separation that can occur in such a shampoo, and the use of the particularly preferred cellulosic thickener to retard phase separation at a relatively high concentration of myristyl myristate.

Example 3: Study of Physical Properties of Shampooed Hair

Physical properties of hair treated with a shampoo of this invention were compared to the same properties of hair treated with a similar shampoo that did not contain a pearlescent ester useful herein.

The shampoo compositions used in this comparison were prepared in a manner similar to the shampoo of Example 1. These compositions had substantially the same ingredients, pH value and viscosity as did Shampoo A of Example 2, with the addition of 0.05 weight percent 2-hydroxy-4-methoxybenzophenone-5-sulfonic acid to both compositions. The shampoo of this invention (Shampoo I) also contained 0.60 weight percent myristyl myristate. The additions of the benzophenone derivative in both the control shampoo (Shampoo J) and Shampoo I, and the myristyl myristate in Shampoo I were made by reducing the amount of water in Shampoo A by the appropriate amounts. A commercially available shampoo (Shampoo K) was used as a second control for two of the comparisons.

The physical properties examined included the following: (1) hair fiber tensile properties; (2) combing properties; (3) static on the hair; and (4) product add-on. The results of these comparisons are discussed below.

1. Hair Fiber Tensile Properties

Hair fiber tensile properties were measured using an Instron Universal Testing Instrument, Model 1122 manufactured by Instron Corporation of Canton, Mass. The hair samples utilized were both bleached and waved, and were purchased as such from De Meo Brothers of New York, Lot 81-D2.

Hair for all treatments was made into tresses about six inches long. Each tress was shampooed with 1 milliliter of shampoo, rinsed under tepid, running water for about 15 seconds, shampooed again with the same shampoo, rinsed again for 1 minute and then dried. The dried tresses were then equilibrated at 24° C. and 42 percent relative humidity. A three inch segment was thereafter cut from the middle of a fiber and weighed accurately. Each cut fiber was then mounted between two tabs so that the fiber length between tabs was 2 inches. The mounted fibers were then equilibrated for about 18 hours at 23° C. and 56 percent relative humidity. The tabbed fibers so equilibrated were placed between the two grips of the Instron Universal Testing Instrument, with the grips being extended at constant speed until rupture.

Break elongation was measured in inches by the increase in gage length measured after rupture, gage travel stopping at rupture. Break stress is a measure of the load on a fiber at break divided by fiber denier and was reported in units of gram per denier. Break strain was calculated as the increase in gage length after break divided by the initial gage length times 100 percent.

A total of 21 individual fibers were compared for each treatment used. Statistical means and standard deviations were calculated for groups of similarly treated fibers with results being compared by the Student's test.

Comparisons of break elongation, break stress and break strain all showed increases for the shampoo of this invention (Shampoo I) when compared to the similar shampoo without myristyl myristate (Shampoo J). These results were significant at the 90 percent confidence level, or greater.

The comparison of Shampoo I of this invention to the commercially available product (Shampoo K) also showed an increase in break stress at the 90 percent confidence level. Break elongation and break strain also showed increases for Shampoo I over Shampoo K, but the level of confidence was less than 90 percent for each comparison.

Comparisons for each determination between the commercial shampoo (Shampoo K) and Shampoo J showed decreases that were not significant at the 90 percent confidence level, or more.

2. Combing Properties

Combing properties were measured along the above-described instrument with a hair tress affixed to the stationary member and a comb affixed to the moving member of the instrument to provide a means for mechanical combing. Brown hair (Lot 81-3) from De Meo Brothers and the same bleached and waved hair used for tensile measurements were utilized.

Tresses were first wet thoroughly and then combed mechanically six consecutive times to provide initial wet combing data. The tresses were then paired, based on wet peak load values (discussed below), dried and equilibrated at 25° C. and 60 percent relative humidity. Six consecutive mechanical combings on each of the paired, equilibrated tresses provided initial dry combing measurements.

The paired tresses were then shampooed with either Shampoo I or Shampoo J using the technique discussed in Section 1 of this Example.

After treatment wet combing measurements on the paired tresses were then made using six consecutive mechanical combings per tress. The paired tresses were dried, equilibrated again at 25° C. and 60 percent relative humidity and then combed mechanically six consecutive times per tress, as had been done for the prior measurements, to provide after treatment dry combing measurements.

Combing properties measured were peak load which is the highest load in grams that was recorded during combing of the tress. Average load was determined from seven readings taken during each combing stroke, the comb being moved about three-quarters of one inch down the tress to produce each of the seven readings. Each combing was repeated six times for each tress combed. Since two tresses were for each combing condition, the average load was an average of eighty-four readings. Average load was reported in grams taken along the tress from root to tip. The third measurement was total energy of combing which was determined from the area under the load versus distance curve as plotted by the machine and measured from the hair root to tip in units of centimeter-gram force. Data were analyzed using the Student's t test.

The comparisons showed that for wet combing of brown hair, there was no difference reliable at the 90 percent confidence level, or more, when initial values were compared to values from Shampoo J for peak load and total energy. Values were increased at at least a 90 percent confidence level when Shampoo I was compared to the initial value or Shampoo J for peak load, average load and total energy.

Dry combing of the brown hair tresses showed no differences between the treatments that were significant at the 90 percent confidence level, or more.

Wet combing of bleached-waved hair showed that the average load for combing the Shampoo I treated hair was greater than that for Shampoo J at a confidence level above 90 percent. None of the other comparisons showed differences that were significant at the 90 percent confidence level, or more.

Dry combing of bleached-waved hair showed that peak load, average load and total energy were reliably greater for Shampoo I than for Shampoo J at the 90 percent confidence level, or more. Total energy values for both shampoo treatments were also higher than the initial values at the 90 percent confidence level, or more. The remaining comparisons were not significantly different at the 90 percent confidence level.

The increases in force to comb hair demonstrated by the above comparisons are believed to be advantageous for fine, limp hair where the increased combing force may be perceived as an imparting of body.

3. Static Control

Bleached-waved and normal brown hair tresses treated with Shampoos I and J as discussed in Sections 1 and 2 were dried and equilibrated at 25° C. and 60 percent relative humidity, and then combed mechanically 50 times on the Instron Universal Testing Instrument at a pre-set rate of speed. The static charge so produced was measured using a Keethly Static Maker.

The results showed no difference in static between hair shampooed with either shampoo.

4. Weight Gain After Shampooing

Twelve bleached-waved hair tresses were divided into three groups after equilibration at 25° C. and 60 percent relative humidity, and subsequent accurate weighing of each tress to four decimal places. Each group of tresses was then treated as discussed in Sections 1-3 using either of Shampoos I, J or K (the commercial product).

After drying and re-equilibration under the previously used conditions, each group of tresses showed a slight decrease in weight that was not signiicant at the 90 percent confidence level, or more.

Example 4: Stable Shampoos With High Levels of Myristyl Myristate

Two shampoos (L and M) were prepared containing elevated levels of myristyl myristate following the method of preparation used in Example 1. The compositions contained the following ingredients.

| Ingredient | Weight Percent | |
|---|---|---|
| | Shampoo L | Shampoo M |
| Water | Q.S. to 100 | Q.S. to 100 |
| Cellulosic thickener | 0.60 | 0.60 |
| Tetrasodium ethylenediamine-tetracetate | 0.15 | 0.15 |
| Ammonium chloride | 1.90 | 1.90 |
| Ammonium lauryl sulfate (30 percent active) | 50.00 | 50.00 |
| Fatty acid diethaolamide[2] | 3.00 | 3.00 |
| Myristyl myristate | 1.75 | 2.00 |
| Perfume | 0.25 | 0.25 |
| Colorant | Q.S. | Q.S. |
| Preservative | Q.S. | Q.S. |
| Citric Acid (50 percent active) | Q.S. | Q.S. |
| | 100.00 | 100.00 |

[1]The cellulosic thickener used was METHOCEL JSMS sold by The Dow Chemical Company.
[2]N,N—(2-hydroxyethyl)coco fatty acid amide was used.

Each shampoo had a pH value of 6.1–6.3 and developed pearlescence within eight hours of preparation. Each of the shampoos remained stable to separation for more than three weeks. Shampoo L had a viscosity of 2000 centipoises on preparation, while Shampoo M had a viscosity of 1900 centipoises on preparation. Both shampoos exhibited an increase in viscosity on the day after their preparation.

Example 5: Shampoos Containing Alternative, Potential Pearlescing Agents

Two further shampoos (N and O) were prepared to assess two potential pearlescing agents, cetyl palmitate and cetyl lactate. Shampoo J of Example 3 was used as the base formula to which 1.2 weight percent cetyl palmitate (Shampoo N) or 1.0 weight percent cetyl lactate (Shampoo O) were added in the place of an equal, respective, amount of water.

Shampoos N and O were prepared by a method analogous to the method utilized for the shampoo of Example 1 wherein cetyl palmitate or cetyl lactate was used to replace myristyl myristate.

In the case of cetyl palmitate, Shampoo N, an opaque shampoo resulted which showed no pearlescence. Shampoo O, that contained cetyl lactate, was clear after several days, and also showed no pearlescence.

The present invention has been described with respect to preferred embodiments. It will be clear to those skilled in the art that modifications and/or variations of the disclosed compositions and methods can be made without departing from the scope if the invention set forth herein. The invention is defined by the claims that follow.

What is claimed is:

1. In an improved pearlescent shampoo containing water and an effective amount of a cleansing, surface active agent wherein the improvement comprises myristyl myristate present in a crystalline state and in an amount of about 0.2 to about 2.5 weight percent as the pearlescing agent.

2. The pearlescent shampoo according to claim 1 wherein said myristyl myristate is present in an amount of about 0.25 to about 2.0 weight percent.

3. The pearlescent shampoo according to claim 1 additionally including about 0.25 to about 1.5 weight percent of water-dispersible alkyl and hydroxyalkyl substituted polysaccharide wherein the alkyl substituent is selected from the group consisting of methyl and ethyl and the hydroxyalkyl substituent is selected from the group consisting of 2-hydroxyethyl, 2-hydroxypropyl and 2-hydroxybutyl.

4. The pearlescent shampoo according to claim 1 wherein said cleansing, surface active agent is anionic and is present in an amount of about 7 to about 17 weight percent of the shampoo.

5. The pearlescent shampoo according to claim 4 wherein said cleansing, surface active agent is selected from the group consisting of an alkali metal and ammonium salt of a fatty alkyl sulfate, a fatty alpha-olefin sulfonate, and mixtures thereof.

6. A pearlescent shampoo comprising water, about 7 to about 17 weight percent of an anionic surface active agent that is selected from the group consisting of an alkali metal and an ammonium salt of a fatty alkyl sulfate, a fatty alpha-olefin sulfonate and mixtures thereof, about 0.25 to about 4 weight percent N,N-bis(2-hydroxyethyl)amide of a fatty acid, and about 0.2 to about 2.5 weight percent of myristyl myristate.

7. The pearlescent shampoo according to claim 6 additionally including about 0.5 to about 1 weight percent of a water-dispersible alkyl and hydroxyalkyl substituted polysaccharide wherein the alkyl substituent is selected from the group consisting of methyl and ethyl and the hydroxyalkyl substituent is selected from the group consisting of 2-hydroxyethyl, 2-hydroxypropyl and 2-hydroxybutyl.

8. The pearlescent shampoo according to claim 7 wherein said water-dispersible alkyl and hyroxyalkyl substituted polysaccharide is a cellulose derivative containing methyl and 2-hydroxypropyl substituents on the cellulose anhydroglucose rings.

9. The pearlescent shampoo according to claim 6 wherein said myristyl myristate is present in an amount of about 0.25 to about 2 weight percent.

10. A method for preparing an improved pearlescent shampoo which comprises:
providing a liquid medium containing water and an amount of a surface active agent effective for cleansing;
wherein the improvement comprises admixing myristyl myristate in an amount of 0.2 to about 2.5 weight percent of said shampoo with said liquid medium while said myristyl myristate is in a liquid state to form a substantially homogeneous, substantially visible light transparent admixture; and
reducing the temperature of said admixture to ambient temperature to form a pearlescent shampoo having said myristyl myristate in crystalline form.

11. The method according to claim 10 wherein said myristyl myristate is present in an amount of about 0.25 to about 2.0 weight percent of said shampoo.

12. The method according to claim 10 wherein said myristyl myristate is heated to a temperature greater than its melting point prior to said admixture.

13. The method according to claim 12 wherein said liquid medium is heated to a temperature greater than the melting point of said myristyl myristate prior to said admixture.

14. The method according to claim 10 wherein said liquid medium additionally contains about 0.25 to about 1.5 weight percent of water-dispersible derivative of cellulose having alkyl and hydroxyalkyl substituents on the cellulose anhydroglucose rings wherein the alkyl substituent is selected from the group consisting of methyl and ethyl and the hydroxyalkyl substituent is selected from the gorup consisting of 2-hydroxyethyl, 2-hydroxypropyl and 2-hydroxybutyl.

15. The method according to claim 10 wherein said surface active agent is selected from the group consisting of an alkali metal and an ammonium salt of a fatty alkyl sulfate, a fatty alpha-olefin sulfonate and mixtures thereof, and is present at about 5 to about 20 weight percent of said pearlescent shampoo.

16. A method for preparing an improved pearlescent shampoo which comprises:

providing a liquid medium containing water, about 7 to about 17 weight percent of a surface active agent that is selected from the group consisting of an alkali metal and an ammonium salt of lauryl sulfate, a fatty alpha-olefin sulfonate prepared from mixed olefins having about 12 to about 14 carbon atoms in the fatty chain and mixtures thereof, and about 0.5 to about 1 weight percent or a water-dispersible cellulose derivative containing methyl and 2-hydroxypropyl substituents on the cellulose anhydroglucose rings; wherein the improvement comprises admixing myristyl myristate with said liquid medium while said myristyl myristate is in a liquid state to form a substantially homogeneous, substantially visible light transparent admixture, the amount of myristyl myristate being about 0.25 to about 2 weight percent of the total shampoo; and reducing the temperature of said admixture to ambient temperature to form a pearlescent shampoo having said myristyl myristate in crystalline form.

17. A method for retarding phase separation in an improved pearlescent shampoo wherein the improvement comprises about 1 to about 2.5 weight percent myristyl myristate as the pearlescent agent comprising admixing as a phase stabilizing ingredient about 0.25 to about 1.5 weight percent of a water-dispersible derivative of cellulose containing methyl and 2-hydroxypropyl substituents on the cellulose anhydroglucose rings into said shampoo to form a substantially homogeneous admixture.

* * * * *

UNITED STATES PATENT AND TRADEMARK OFFICE
CERTIFICATE OF CORRECTION

PATENT NO. : 4,438,096

DATED : March 20, 1984

INVENTOR(S) : John C. Preston

It is certified that error appears in the above-identified patent and that said Letters Patent is hereby corrected as shown below:

Column 9, line 16, --t-- should be inserted after "dent's";

Column 9, line 35, "along" should be --using--;

Column 13, line 16, "or" should be --of--.

Signed and Sealed this

Third Day of December 1985

[SEAL]

Attest:

DONALD J. QUIGG

Attesting Officer

Commissioner of Patents and Trademarks